US011993764B2

(12) United States Patent
Heller et al.

(10) Patent No.: US 11,993,764 B2
(45) Date of Patent: May 28, 2024

(54) DEVICES FOR STUDYING PLANT-FUNGUS INTERACTIONS AND FOR IMAGING PLANT ROOTS

(71) Applicants: The Regents of the University of California, Oakland, CA (US); National Technology & Engineering Solutions of Sandia, LLC, Albuquerque, NM (US)

(72) Inventors: Jens Heller, Berkeley, CA (US); Lauren Jabusch, Emeryville, CA (US); Peter Kim, Alameda, CA (US); Trent Northen, Walnut Creek, CA (US); N. Louise Glass, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 613 days.

(21) Appl. No.: 16/886,849

(22) Filed: May 29, 2020

(65) Prior Publication Data

US 2020/0385663 A1 Dec. 10, 2020

Related U.S. Application Data

(60) Provisional application No. 62/857,604, filed on Jun. 5, 2019.

(51) Int. Cl.
*C12M 1/12* (2006.01)
*C12M 1/00* (2006.01)

(52) U.S. Cl.
CPC ............ *C12M 23/34* (2013.01); *C12M 23/22* (2013.01); *C12M 25/02* (2013.01)

(58) Field of Classification Search
CPC ........ C12M 23/34; C12M 23/22; A01G 18/60
USPC ................ 206/423; 47/32.7, 32.8, 65.5, 65.7
See application file for complete search history.

(56) References Cited

U.S. PATENT DOCUMENTS

| | | | |
|---|---|---|---|
| 9,975,118 B2 * | 5/2018 | Deutsch | C12M 23/22 |
| 10,787,639 B2 | 9/2020 | Gao et al. | |
| 2008/0141585 A1 * | 6/2008 | Benfey | A01G 9/02 |
| | | | 47/32.7 |
| 2019/0241854 A1 * | 8/2019 | Hagihara | C08G 73/1007 |
| 2019/0264156 A1 * | 8/2019 | Hagihara | C12N 1/00 |
| 2020/0275618 A1 * | 9/2020 | Akhtman | A01M 21/043 |
| 2021/0259169 A1 * | 8/2021 | Valiquette | G06V 20/188 |

(Continued)

OTHER PUBLICATIONS

Massalha et al., "Live imaging of root-bacteria interactions in a microfluidics setup," Proceedings of the National Academy of Sciences, vol. 114, No. 17, pp. 4549-4554, Apr. 25, 2017.

(Continued)

*Primary Examiner* — Jacob K Ackun (57) ABSTRACT

This disclosure provides systems, methods, and apparatus related to the determination of ecological processes. In one aspect, a device includes a base and a substrate in contact with a first side of the base. The base defines a stem port. The substrate and the first side of the base define a chamber. The chamber includes a root chamber and a first nutrient chamber. The root chamber and the first nutrient chamber are separated by a first mesh having openings of about 1 micron to 300 microns. The device is operable to house a plant, with roots of the plant being in the root chamber, and a stem of the plant passing through the stem port.

10 Claims, 11 Drawing Sheets

(56) References Cited

U.S. PATENT DOCUMENTS

2023/0225329 A1\* 7/2023 Kong .................... A01N 63/20
                                                    504/117

OTHER PUBLICATIONS

Aufrecht et al., "Quantifying the Spatiotemporal Dynamics of Plant Root Colonization by Beneficial Bacteria in a Microfluidic Habitat," Advanced Biosystems, vol. 2, pp. 1800048 (1 of 12), 2018.

Rellan-Alvarez et al., "GLO-Roots: an imaging platform enabling multidimensional characterization of soil-grown root systems," Elife, https://doi.org/10.7554/eLife.07597.002, pp. 1-26, Aug. 19, 2015.

Uehling et al., "Microfluidics and Metabolomics Reveal Symbiotic Bacterial-Fungal Interactions Between Mortierella elongata and Burkholderia Include Metabolite Exchange," Frontiers in Microbiology, vol. 10, Article 2163, pp. 1-13, Oct. 1, 2019.

Aleklett et al., "Build your own soil: exploring microfluidics to create microbial habitat structures," The ISME Journal, vol. 12, pp. 312-319, Nov. 14, 2017.

Aufrecht et al., "Imaging the Root Hair Morphology of *Arabidopsis* Seedlings in a Two-layer Microfluidic Platform," Journal of Visualized Experiments, vol. 126, pp. 1-7, Aug. 15, 2017.

Gao et al., "Ecosystem Fabrication (EcoFAB) Protocols for The Construction of Laboratory Ecosystems Designed to Study Plant-microbe Interactions," Journal of Visualized Experiments, vol. 134, pp. 1-16, Apr. 10, 2018.

Millet et al., "Increasing access to microfluidics for studying fungi and other branched biological structures, " Fungal Biology and Biotechnology, vol. 6, No. 8, pp. 1-14, 2019.

\* cited by examiner

DEVICES FOR STUDYING PLANT-FUNGUS INTERACTIONS AND FOR IMAGING PLANT ROOTS

RELATED APPLICATIONS

This application claims priority to U.S. Provisional Patent Application No. 62/857,604, filed Jun. 5, 2019, which is herein incorporated by reference.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure relates generally to the field of determining ecological processes, and more particularly to determining plant-microbe interactions.

BACKGROUND

A program to interrogate the function of soil microbiomes with implications for carbon cycling and sequestration, nutrient availability, and plant productivity in natural and managed ecosystems is being performed to derive a mechanistic understanding of fungal contributions to mineral accessibility in marginal soils. Precisely controlled ecosystem fabrications (EcoFABs) can be used for creating and manipulating plant-microbe interactions under specific environmental conditions. In some embodiments, an EcoFAB system and devices include sterile plant growth chambers attached to a microscope slide. This set-up enhances studying the impact of microbes on plant growth phenotypes. EcoFAB systems and devices are described in U.S. patent application Ser. No. 15/963,887, filed Apr. 26, 2018, which is herein incorporated by reference.

In plants, phosphorus drives biological reactions and is essential for growth. Phosphorus facilitates root formation, reproductive development, and synthesis of proteins. Phosphorus is one of the most limited nutrients for plants in the environment because the form that is preferentially assimilated, inorganic phosphate, is unevenly distributed in soils and greater than 80% of organic phosphate is not readily available to roots. In the environment, phosphorus is primarily present as insoluble iron and aluminum phosphates in acidic soils or calcium phosphates in alkaline soils.

High-resolution microscopy is a tool for examining microbes. However, the area around roots where microbial-plant interaction is highest is difficult to examine. The opacity of soil and irregular growth pattern of the roots leads to challenges in sampling and examination. For example, greenhouse pots, hydroponic pots, and agar seedling plates are difficult to analyze by microscopy without dissection and mounting on slides. However, in vivo microscopy would allow for time series microscopy without removal or disruption of microbial species or root structures.

BRIEF DESCRIPTION OF THE DRAWINGS

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

The terms "about" or "approximate" and the like are synonymous and are used to indicate that the value modified by the term has an understood range associated with it, where the range can be ±20%, ±15%, ±10%, ±5%, or ±1%. The terms "substantially" and the like are used to indicate that a value is close to a targeted value, where close can mean, for example, the value is within 80% of the targeted value, within 85% of the targeted value, within 90% of the targeted value, within 95% of the targeted value, or within 99% of the targeted value.

Numerous microorganisms—especially those associated with roots—have the ability to increase plant growth and productivity. For example, filamentous fungi of the genus *Trichoderma* are among those microbes and the most commonly studied natural bio-control agents. Some *Trichoderma* species have been shown to protect plants against biotic and abiotic stresses and to promote plant growth by increasing nutrient uptake. Their potential in solubilization of otherwise unavailable mineral nutrients is under investigation. Using EcoFAB devices, it is possible to spatially separate phosphorus sources and plant roots. It has been demonstrated that *Trichoderma harzianum* promotes plant growth in the presence of insoluble $AlPO_4$. Importantly, this effect was only evident when *T. harzianum* was inoculated close to the $AlPO_4$ source, whereas no growth promotion was observed when the fungus was inoculated close to the seedling. These data suggest that *T. harzianum* helps to solubilize phosphate and makes it available for plant uptake and utilization.

Another efficient strategy of plants to overcome phosphate limitation is the association of roots with arbuscular mycorrhizal (AM) fungi. Even though these microorganisms form symbiotic associations with nearly 80% of terrestrial plants, research on AM fungi is limited due to the challenging nature of these systems. New methods that facilitate the handling of AM fungi are needed to enhance and enable the research on these beneficial organisms.

Described herein is an EcoFAB device that allows for the study of mycorrhizal plant-fungal interactions. In some embodiments, this EcoFAB device includes a plant growth chamber and compartments for nutrient sources that are separated by a mesh sheet. This set-up effectively prevents plant roots from accessing nutrients if the nutrients are not associated with AM fungi.

EcoFAB devices described herein can be placed in and used in an EcoFAB system. EcoFAB systems are described in U.S. patent application Ser. No. 15/963,887. Briefly, an EcoFAB system can be used to construct model ecosystems (e.g., reproducible or simplified ecosystems) to enable controlled, replicated laboratory experiments investigating plant-microbe interactions to generate insights that can be further tested in larger scale or in the field. In some embodiments, an EcoFAB system can mimic growth conditions, such as soil-filled pots or on agar slabs within greenhouses or incubators, or below-ground conditions (e.g., to study below-ground processes, such as rhizosphere metabolites in soil). In some embodiments, an EcoFAB system can be used to monitor and manipulate plant growth environments in a precise, controlled, and/or reproducible manner.

Embodiments of the EcoFAB devices described below can be used to facilitate manipulation of nutrient distributions. The devices allow for control the spatial distribution and availability of nutrients. For example, adding *T. harzianum* to an insoluble phosphate source increases B. distachyon dry weight yield. The point of microbe inoculum determines efficiency.

Embodiments of the EcoFAB devices described below can be iteratively improved and rapidly prototyped. 3-D printing enables going from a concept to the working prototype device in about one week. The insertion of a porous membrane with less than about 40 micron pores allows for selectively preventing the root system from penetrating while allowing fungal hyphae to cross and nutrients to diffuse. 3-D printed clamps can be used to sandwich the device. The clamps can be machine-milled on a metal sheet for stronger support. The clamps can also be a thick plastic sheet (e.g., acrylic). This also allows for autoclave sterilization. Assembled devices can be inserted in a sterile enclosure and connected to an automated watering system, Embodiments of the EcoFAB devices described below can facilitate the establishment of mycorrhizal interactions. The devices for the separation of roots from any given nutrient source. By preventing roots from accessing essential nutrient sources, plants can be forced reliably into mycorrhizal interactions. This enables the study of the effect of mycorrhizal fungi on plant phenotypes Embodiments of the EcoFAB devices described below can facilitate in vivo imaging of mycorrhiza infected roots. The device can be used for noninvasive imaging of whole root systems. Further, time course experiments over several weeks are possible.

Figure 1A:
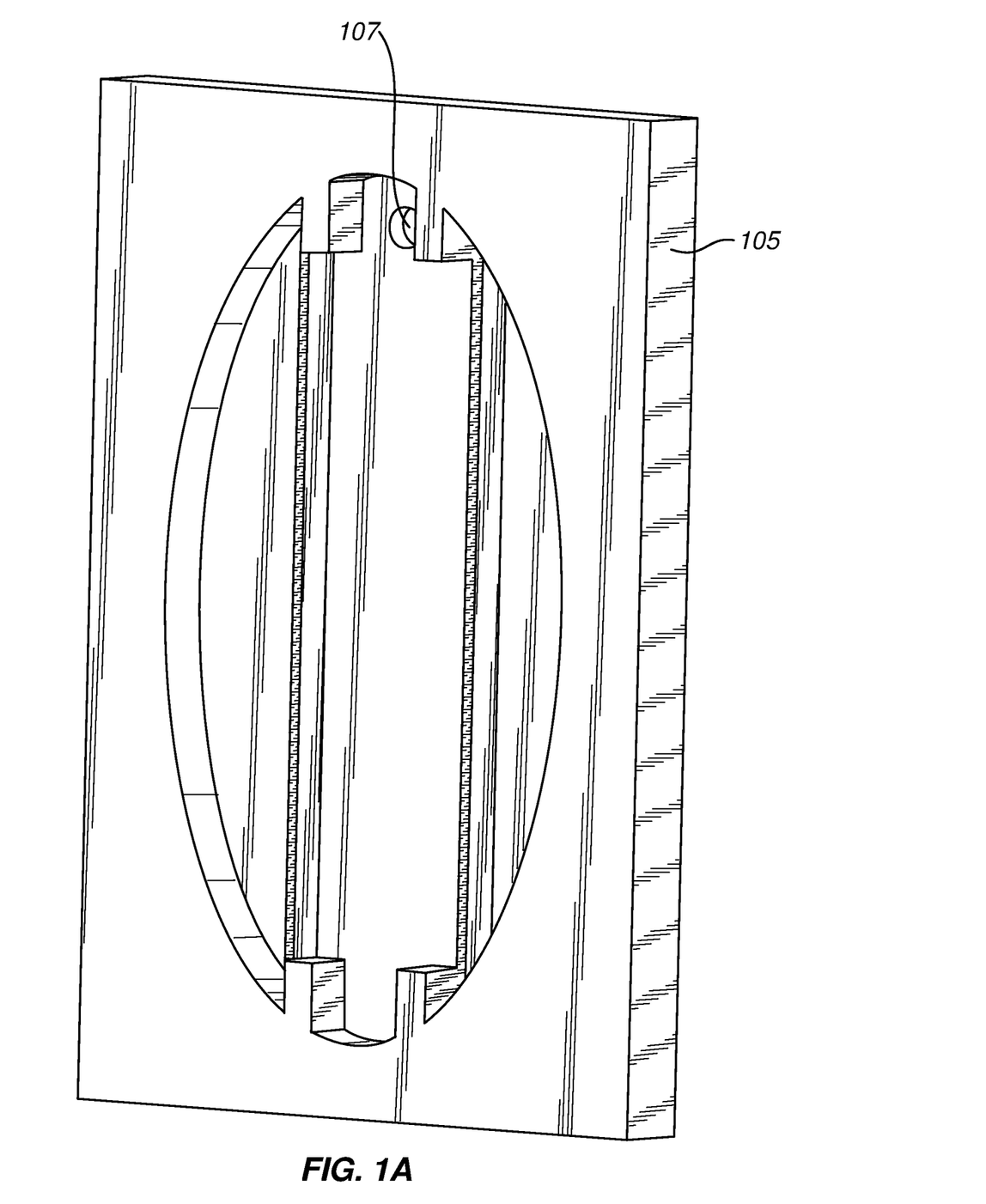
FIGS. 1A and 1B show examples of schematic illustrations of a base of a device.
Figure 1B:
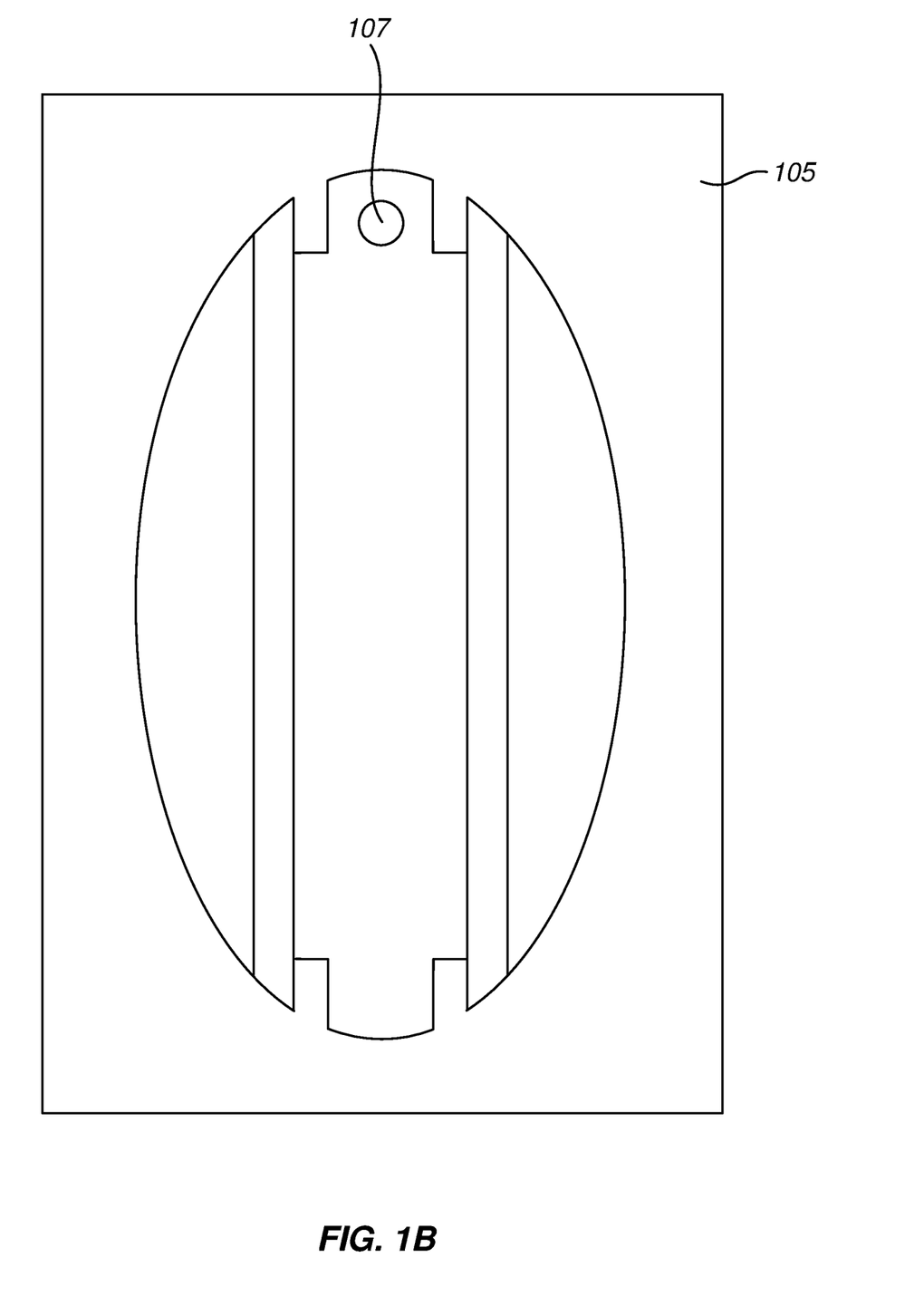
Figure 2A:
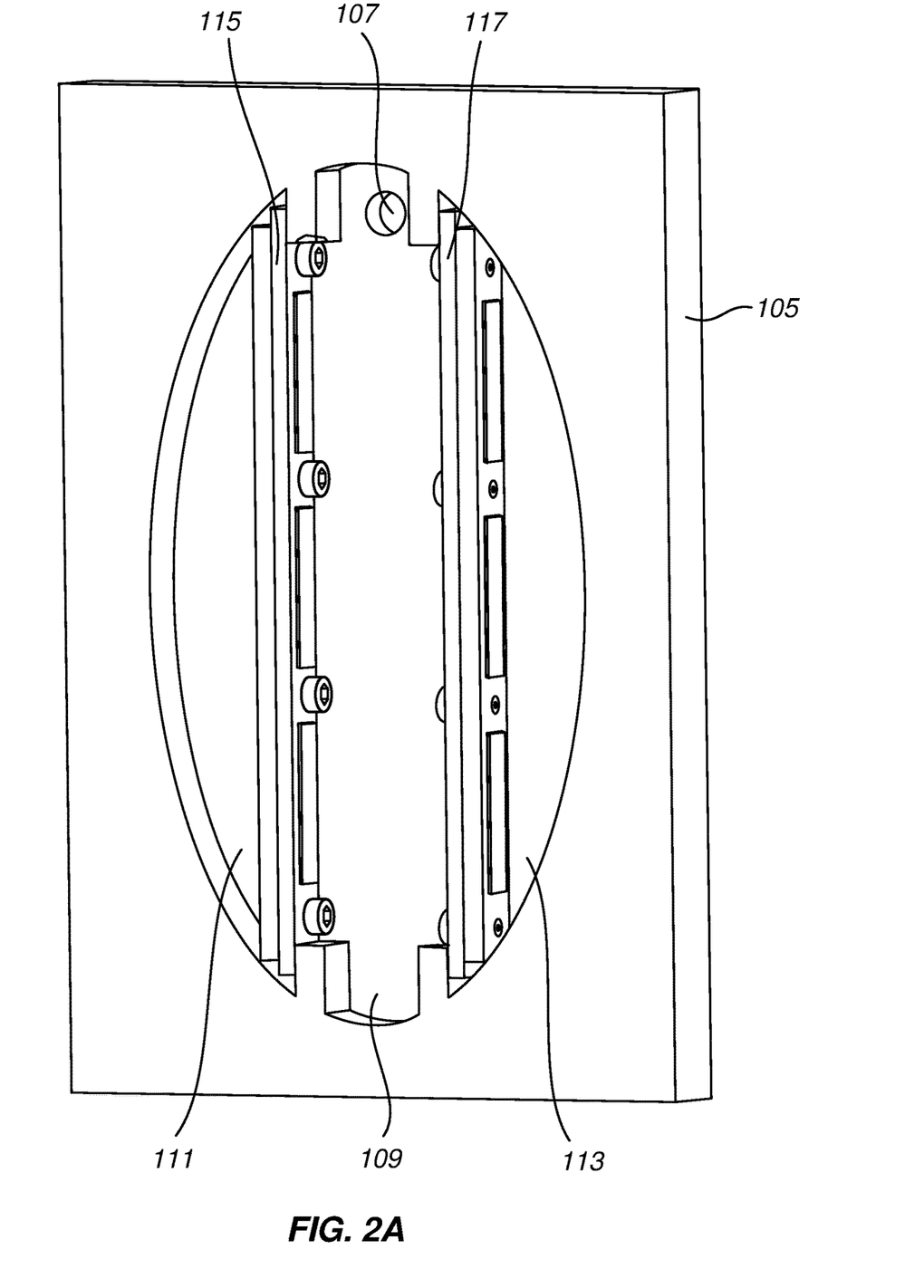
FIGS. 2A and 2B show examples of schematic illustrations of a base of a device including mesh inserts.
Figure 2B:
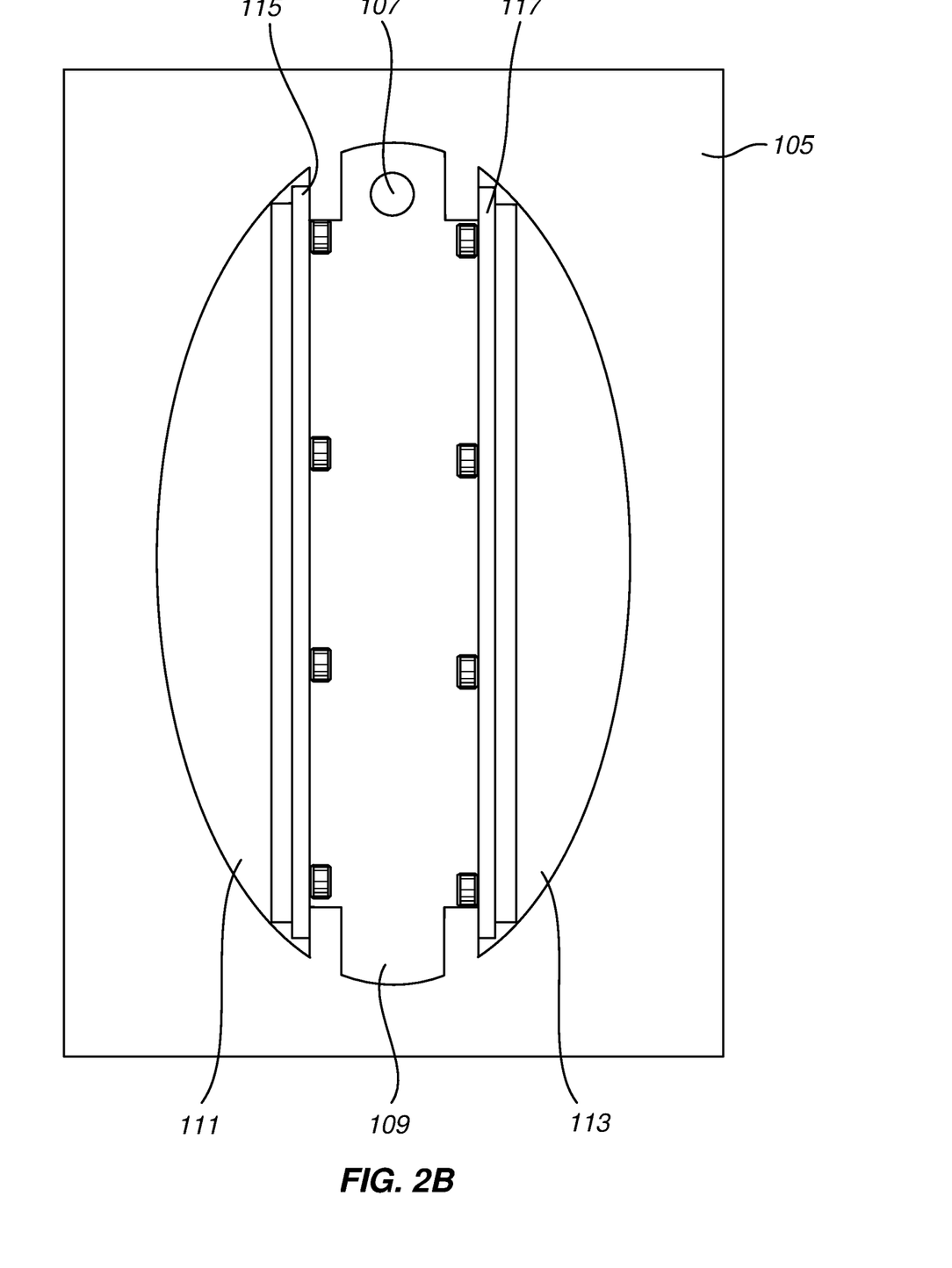
Figure 3A:
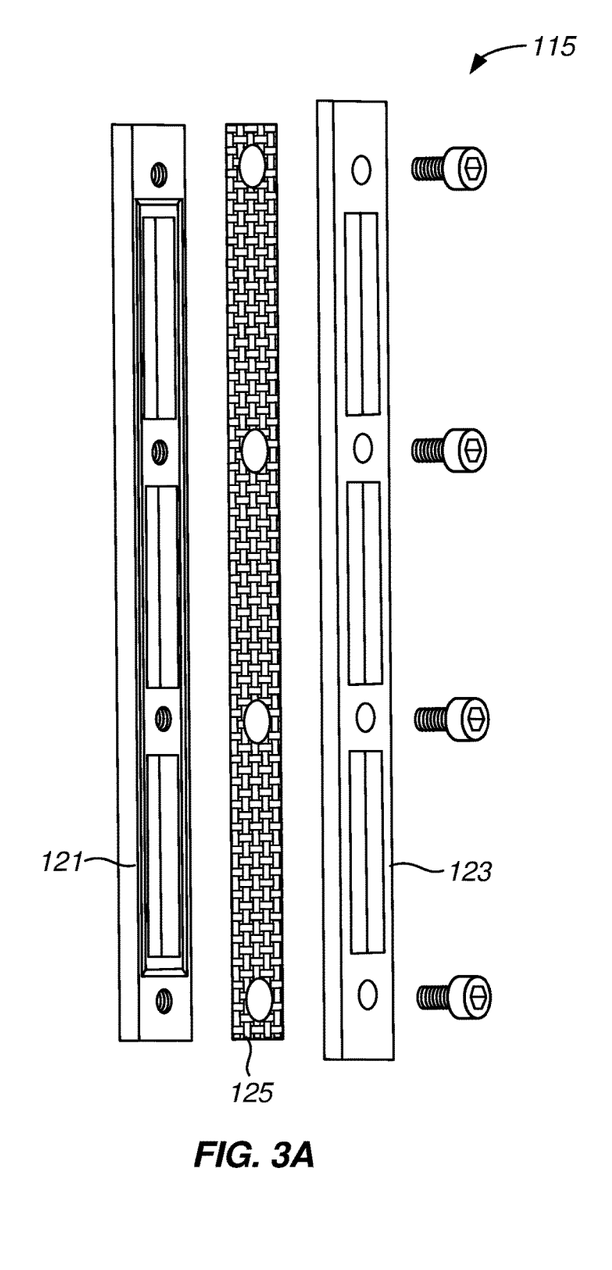
FIGS. 3A and 3B show examples of schematic illustrations of a mesh insert.
Figure 3B:
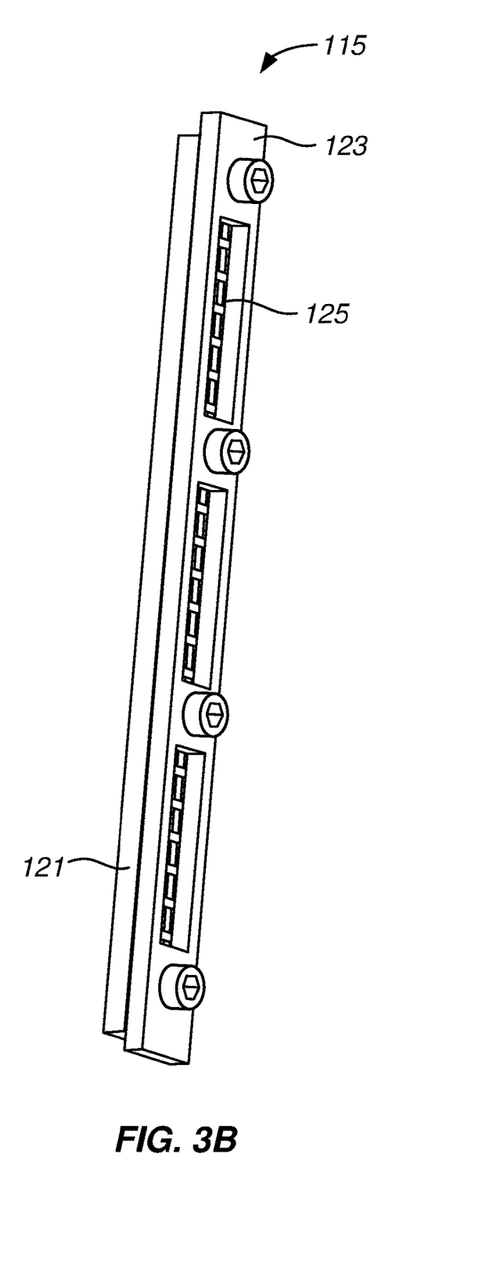
Figure 4:
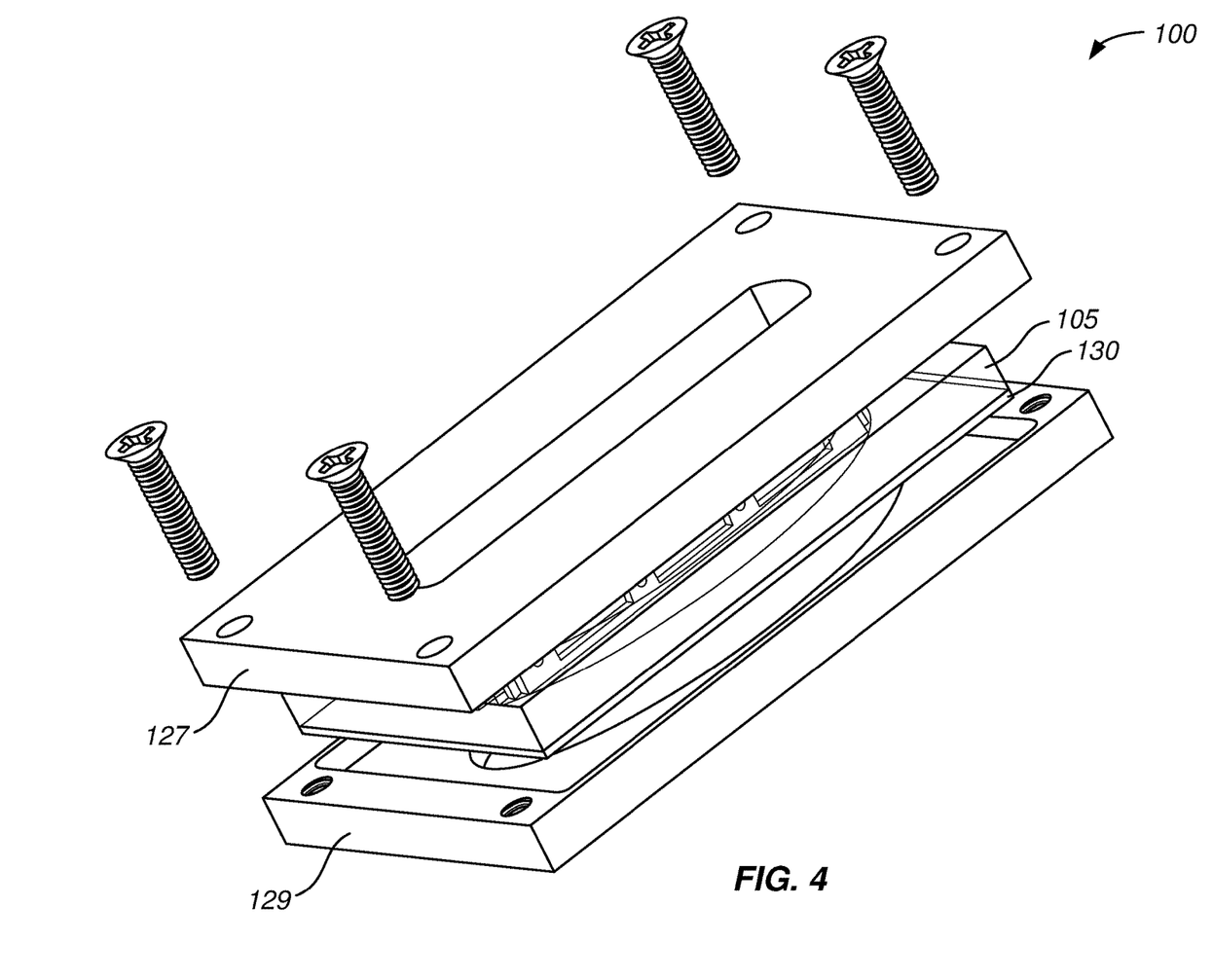
FIG. 4 shows an example of a schematic illustration of a device.
Figure 5:
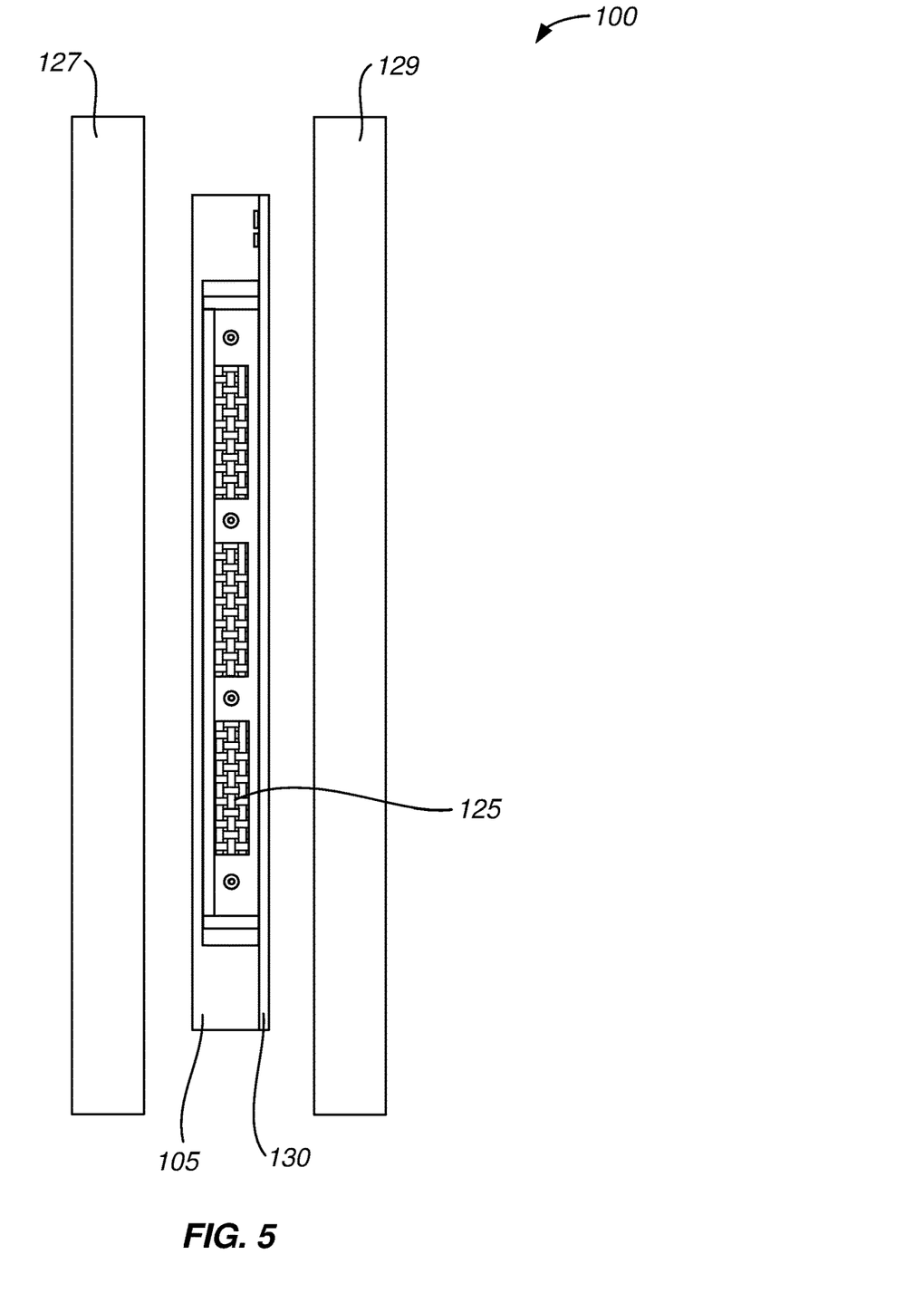
FIG. 5 shows an example of a cross-sectional schematic illustration of a device.

FIGS. 1A and 1B show examples of schematic illustrations of a base of a device. FIGS. 2A and 2B show examples of schematic illustrations of a base of a device including mesh inserts. FIGS. 3A and 3B show examples of schematic illustrations of a mesh insert. FIG. 4 shows an example of a schematic illustration of a device. FIG. 5 shows an example of a cross-sectional schematic illustration of a device.

As shown in FIGS. 1A-5, an EcoFAB device 100 includes a base 105 and a substrate 130 in contact with a first side of the base 105. The base 105 defines a stem port 107. The stem port 107 is a through-hole in the base. In some embodiments, the substrate 130 comprises a flat surface. In some embodiments, the base defines features such than when the substrate 130 is in contact with the first side of the base 105, the substrate 130 and the base 105 define a chamber.

The chamber includes a root chamber 109 and a first nutrient chamber 111, with the root chamber 109 and the first nutrient chamber 111 being separated by a first mesh. In some embodiments, the root chamber 109 and the first nutrient chamber 111 each have a height of about 4 millimeters (mm). The mesh has openings of about 1 micron to 300 microns, or about 40 microns. The device 100 is operable to house a plant, roots of the plant being in the root chamber 109, and a stem of the plant passing through the stem port 107.

In some embodiments, the first mesh is operable to prevent roots from growing into the first nutrient chamber 111, and the first mesh is operable to allow fungi to pass between the first nutrient chamber 111 and the root chamber 109. Solid nutrients may be placed in the first nutrient chamber 111, with no solid nutrients being in the root chamber 109. The plant would not be able to access the solid nutrients, but fungi would be able to access the solid nutrients and pass between the root chamber 109 and the nutrient chamber 111. Thus, the interaction between the plant and the fungi and if the fungi gives the plant access to the nutrients could be studied. The nutrients may be any solid plant nutrients, such as sulfates, phosphorous, and iron.

The size of openings in the first mesh depends on the sizes of the roots of the plant housed in the device. If the plant has thick roots, the mesh may have larger openings. In some embodiments, the first mesh comprises a stainless steel mesh. In some embodiments, the first mesh is housed in a mesh insert 115. As shown in FIGS. 3A and 3B, a mesh insert 115 includes two sides 121 and 123 of a housing and a mesh 125. In some embodiments, the housing 121 and 123 comprises a metal or a plastic.

In some embodiments, a metal (e.g., aluminum) or a plastic (e.g., acrylic) fixture 127 and 129 is used to hold the substrate 130 against the first side of the base 105. In some embodiments, the substrate 130 comprises a sheet of glass (e.g., borosilicate glass). In some embodiments, the substrate 130 is transparent to visible light.

In some embodiments, the dimensions of the base 105 are about 5 centimeters (cm) by about 7.5 cm. In some embodiments, the base is about 5 millimeters (mm) thick. In some embodiments, a diameter of the stem port 107 is about 1 mm to 5 mm, or about 3 mm. In some embodiments, a volume of the root chamber 109 is about 4 milliliters (mL) to 20 mL, about 1 mL to 5 mL, or about 4 mL to 5 mL. In some embodiments, a volume of the nutrient chamber 111 is about 2 mL to 10 mL, about 0.5 mL to 2.5 mL, or about 2 mL to 2.5 mL.

In some embodiments, the device further comprises a gasket (not shown), with the gasket disposed between the base 105 and the substrate 130. In some embodiments, the gasket forms a seal that is not permeable to a liquid.

In some embodiments, the chamber further includes a second nutrient chamber 113, with the root chamber 109 and the second nutrient chamber 113 being separated by a second mesh housed in a mesh insert 117. In some embodiments, the second mesh has the same characteristics as the first mesh. In some embodiments, the second mesh has openings of about 1 micron to 300 microns. When the chamber includes a nutrient chamber 111 and a second nutrient chamber 113, one chamber can be used to house nutrients, and one chamber can be used to inoculate plant roots as a source for mycorrhizal fungus, for example.

In some embodiments, the base 105 comprises a polymer (e.g., polydimethylsiloxane (PDMS)). To fabricate the base 105, a mold for the base can be printed with a three-dimensional printer. The mold can be used to cast the base from a polymer.

As described above, EcoFAB devices can provide a simple, accessible method for studying beneficial plant-soil microbe interactions. Using embodiments described herein, it is possible to use EcoFAB devices to evaluate the effect of beneficial filamentous fungi within the rhizosphere on plant phenotypes. The consequence of spatial distribution of microbes can be investigated. The EcoFAB device to study mycorrhizal fungal-plant interactions enables extensive in vivo imaging of the root without disrupting the mycorrhizal interactions. Using EcoFAB devices, it is possible to measure a direct impact of AM fungi on nutrient access, plant growth, and rhizosphere microbiome associations.

Figure 6A:
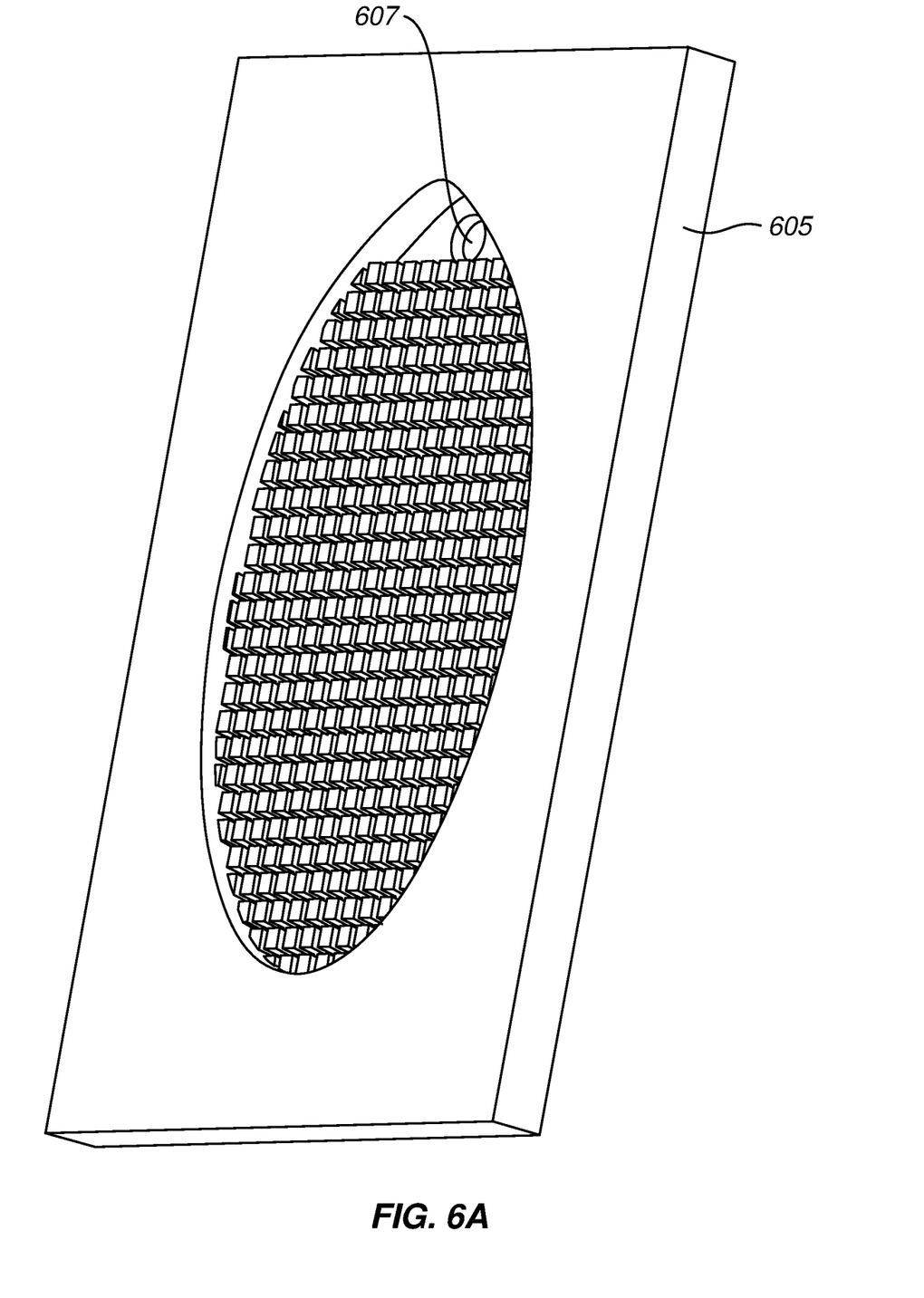
FIGS. 6A and 6B show examples of schematic illustrations of a base of a device.
Figure 6B:
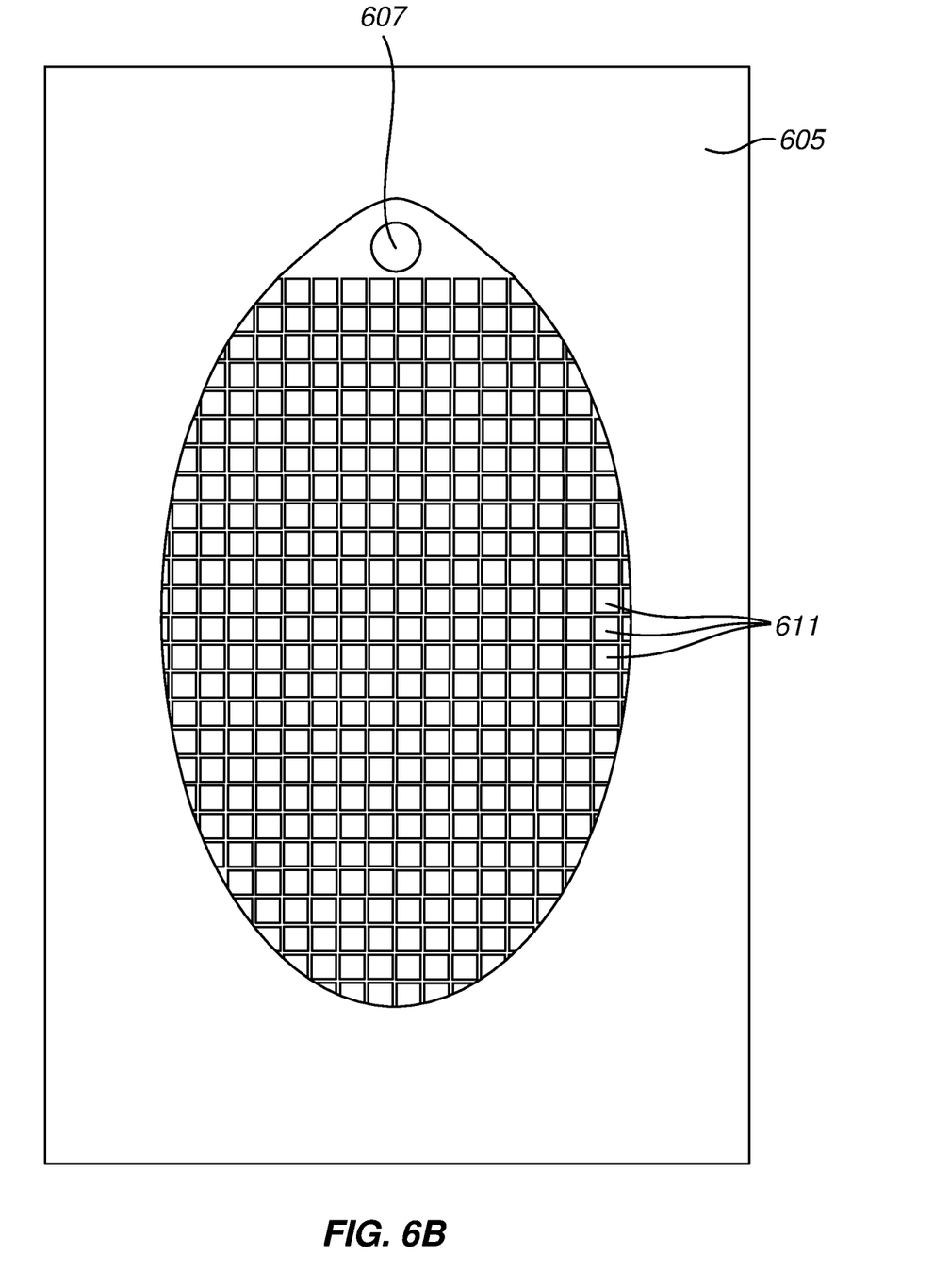
Figure 7:
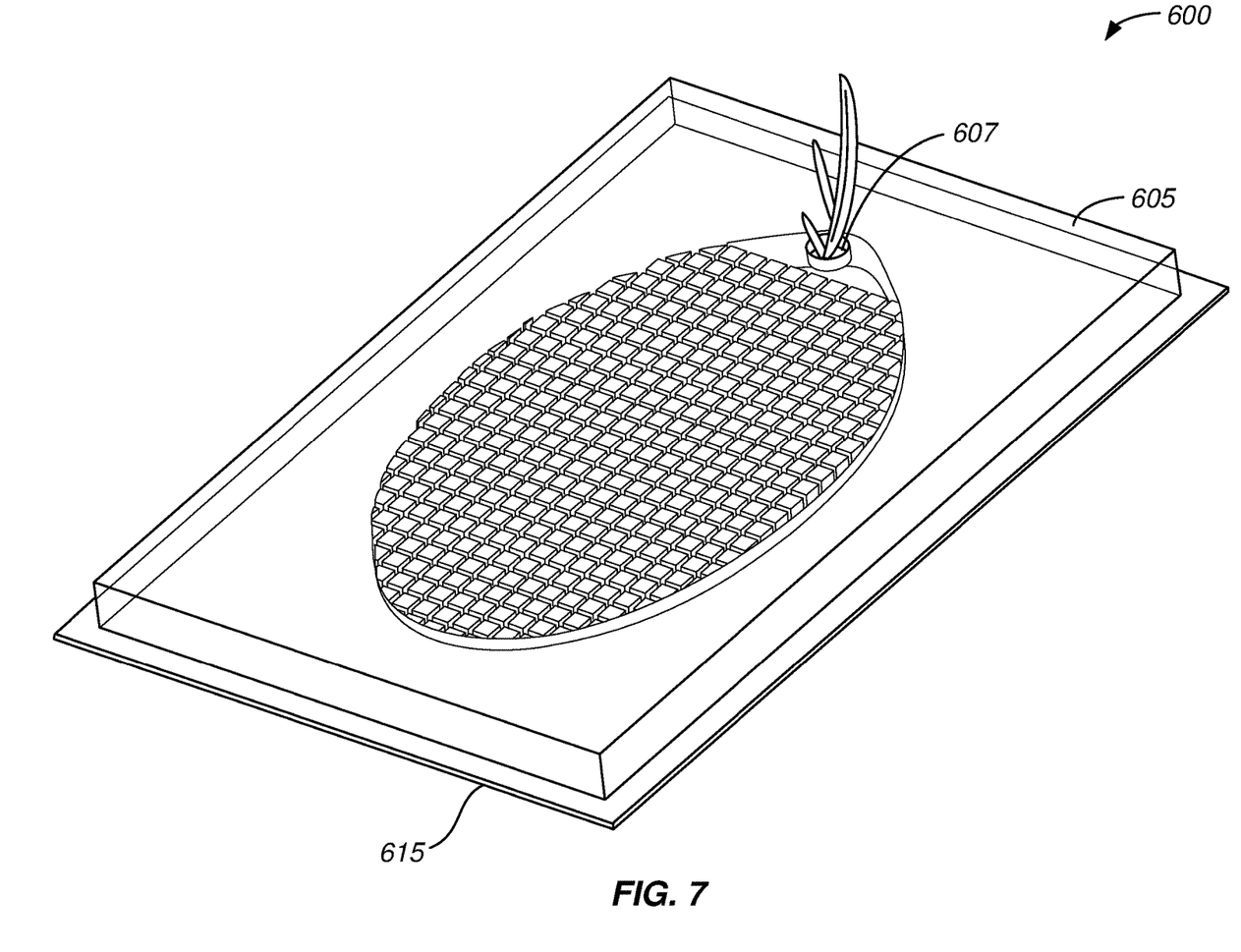
FIG. 7 shows an example of a schematic illustration of a device.
Figure 8:
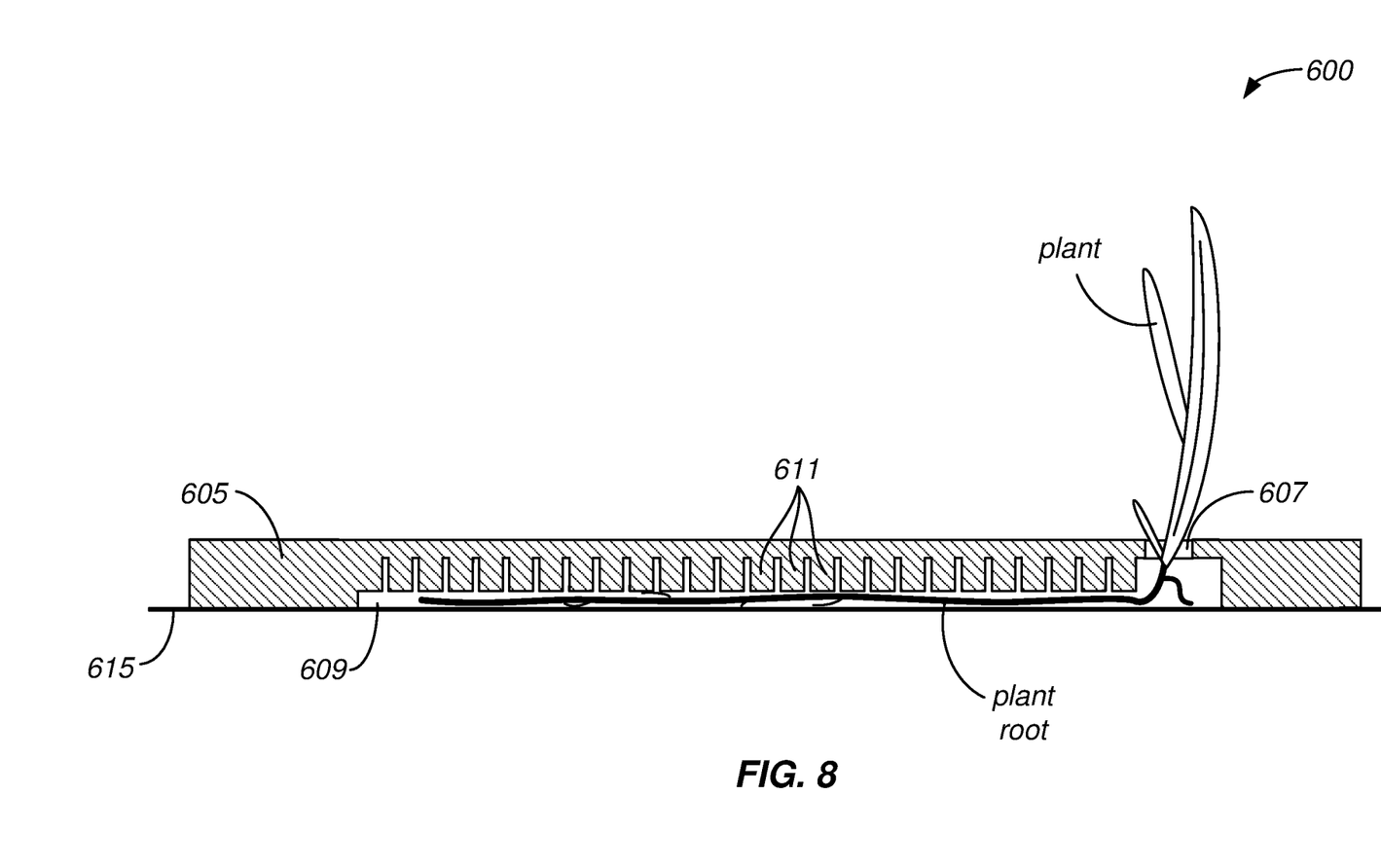
FIG. 8 shows an example of a cross-sectional schematic illustration of a device.

Also described herein is an EcoFAB device that allows for the imaging of plant roots (i.e., for in situ imaging of plant roots). FIGS. 6A and 6B show examples of schematic illustrations of a base of a device. FIG. 7 shows an example of a schematic illustration of a device. FIG. 8 shows an example of a cross-sectional schematic illustration of a device.

As shown in FIGS. 6A-8, an EcoFAB device 600 includes a base 605 and a substrate 615 in contact with a first side of the base 605. The base 605 defines a stem port 607. The stem port 607 is a through-hole in the base. The substrate 615 and the first side of the base 605 define a root chamber 609. The device 600 is operable to house a plant, roots of the plant being in the root chamber 609, and a stem of the plant passing through the stem port 607. The base 605 further defines a plurality of pillars 611 operable to force the roots of the plant to grow proximate the substrate 615.

In some embodiments, the plurality of pillars 611 are arranged on a square grid. In some embodiments, a spacing between a top of a pillar of the plurality of pillars 611 and the substrate 605 is about 0.5 millimeters (mm) to 3 mm, or about 1 mm. Thus, there is a gap between a top of a pillar of the plurality of pillars 611 and the substrate 615. In this gap or spacing, the roots of the plant can grow, with the roots being forced to be flat and to be proximate or close to the substrate 615. In some embodiments, the chamber has a height of about 3 mm. Thus, for a 1 mm spacing, the pillars would have a height of about 2 mm.

In some embodiments, a pillar of the plurality of pillars 611 has a cross-section shape of a square of dimensions of about 0.5 mm to 2 mm by about 0.5 mm to 2 mm, or about 1.5 mm by about 1.5 mm. In some embodiments, a pillar of the plurality of pillars 611 has a cross-section shape of a circle with a diameter of about 0.5 mm to 2 mm, or about 1.5 mm. Other cross-section shapes of the pillars are possible. In some embodiments, a diameter of the stem port 607 is about 1 mm to 5 mm, or about 3 mm.

With the roots proximate or close to the substrate 615, the distance between the roots and a microscope lens on the other side of the substrate 615 (i.e., the side of the substrate that the roots are not proximate or close to) is short. This short distance between the roots and a microscope lens allows high-quality images to be obtained with the microscope.

In some embodiments, a spacing between pillars of the plurality of pillars 611 is about 200 microns to 400 microns, or about 300 microns. This spacing between pillars allows liquid and media to flow between the pillars, allowing water and nutrients to flow among the roots. The spacing is such that the roots cannot grow between the pillars, however.

In some embodiments, the substrate 615 comprises a sheet of glass (e.g., borosilicate glass). In some embodiments, the substrate 615 is transparent to visible light. In some embodiments, the substrate is about 100 microns thick and has dimensions of about 50 mm by about 75 mm.

In some embodiments, the base 605 comprises a polymer (e.g., polydimethylsiloxane (PDMS)). To fabricate the base 605, a mold for the base can be printed with a three-dimensional printer. The mold can be used to cast the base from a polymer. In some embodiments, the first side of the base 605 and the substrate 615 are bonded to one another, with the bond not being permeable to a liquid.

For example, when the base comprises PDMS and the substrate comprises glass, glass-PDMS bonding can be used to bond the substrate to the base. The base can be bonded to the substrate reversibly by placing the substrate on the base after both the substrate and the base are cleaned and treated. The base can be bonded to the substrate irreversibly by placing the substrate on the base after the base is treated with an oxygen (or air) plasma.

CONCLUSION

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A device comprising:
   a base;
   a substrate in contact with a first side of the base, the base defining a stem port, the substrate and the first side of the base defining a chamber, the chamber including a root chamber and a first nutrient chamber, the root chamber and the first nutrient chamber being separated by a first mesh having openings of about 1 micron to 300 microns, and the device operable to house a plant, roots of the plant being in the root chamber, and a stem of the plant passing through the stem port.

2. The device of claim 1, wherein the chamber further includes a second nutrient chamber, and wherein the root chamber and the second nutrient chamber are separated by a second mesh having openings of about 1 micron to 300 microns.

3. The device of claim 1, wherein the first mesh is operable to prevent roots from growing into the first nutrient chamber, and wherein the first mesh is operable to allow fungi to pass between the first nutrient chamber and the root chamber.

4. The device of claim 1, wherein the first mesh comprises a stainless steel mesh.

5. The device of claim 1, further comprising:
a gasket, wherein the gasket is disposed between the base and the substrate.

6. The device of claim 1, wherein the substrate comprises a sheet of glass.

7. The device of claim 1, wherein a diameter of the stem port is about 1 millimeter to 5 millimeters.

8. The device of claim 1, wherein the base comprises a polymer.

9. The device of claim 1, wherein the base comprises polydimethylsiloxane (PDMS).

10. The device of claim 1, wherein a volume of the chamber is about 4 milliliters to 20 milliliters.

* * * * *